United States Patent
Defares et al.

[11] Patent Number: 5,899,203
[45] Date of Patent: May 4, 1999

[54] INTERACTIVE RESPIRATORY REGULATOR

[76] Inventors: Peter Bernard Defares, Emmalaan 9, 3972 EZ Driebergen; Cornelis Adriaan De Willigen, Groen van Prinsterenweg 57, 2221 AC Katwijk; Eduard Theodorus Verveen, Westlandgracht 87/3, 1058 TR Amsterdam, all of Netherlands

[21] Appl. No.: 08/814,088

[22] Filed: Mar. 10, 1997

Related U.S. Application Data

[63] Continuation-in-part of application No. 08/491,946, Aug. 30, 1995, Pat. No. 5,730,145.

[30] Foreign Application Priority Data

Dec. 24, 1992 [NL] Netherlands ............ 9202256

[51] Int. Cl.$^6$ .............. A61M 16/00; A61B 5/02
[52] U.S. Cl. ................. 128/204.23; 128/204.21; 600/529; 600/534
[58] Field of Search ............ 128/204.23, 204.28, 128/204.21; 600/529, 532, 534, 483, 484; 607/20, 28, 30; 601/41

[56] References Cited

U.S. PATENT DOCUMENTS

| | | | |
|---|---|---|---|
| 3,923,055 | 12/1975 | Hammacher | 128/204.23 |
| 4,665,925 | 5/1987 | Leuner et al. | 600/529 |
| 4,686,975 | 8/1987 | Naimon et al. | 128/204.23 |
| 4,895,168 | 1/1990 | Reents | 600/484 |
| 4,966,155 | 10/1990 | Jackson | 600/484 |
| 5,129,390 | 7/1992 | Chopin et al. | 128/204.23 |
| 5,131,399 | 7/1992 | Sciarra | 600/484 |
| 5,201,808 | 4/1993 | Steinhau et al. | 607/20 |
| 5,255,685 | 10/1993 | Parra | 600/483 |
| 5,263,491 | 11/1993 | Thornton | 600/483 |
| 5,520,192 | 5/1996 | Kitney et al. | 600/529 |

*Primary Examiner*—Aaron J. Lewis
*Assistant Examiner*—V. Śrivastava
*Attorney, Agent, or Firm*—Kane, Dalsimer, Sullivan, Kurucz, Levy, Eisele and Richard, LLP

[57] ABSTRACT

An interactive respiratory regulator comprising a recording device recording the respiratory pattern of a user and issuing a corresponding respiratory signal, an instruction signal generator for the generation of an instruction signal that can be perceived by the user in order to influence his respiratory behavior, a control device controlling the instruction signal generator, a processing device which determines by means of a parameter of the respiratory signal received, whether the recorded respiratory pattern during a predetermined time span meets a pre-adjustable standard for this parameter, and which at a certain error percentage sends a starting signal to the control device. The interactive respiratory regulator is characterized in that the processing device processes as parameter the ratio between the in- and exhalation time in a respiratory cycle. In a preferred embodiment the processing device includes the frequency of the respiratory cycles as second parameter and the pre-adjustable standard comprises also a value for this parameter.

15 Claims, 5 Drawing Sheets

INTERACTIVE RESPIRATORY REGULATOR

REFERENCE TO RELATED APPLICATION

This application is a Continuation-in-part of U.S. application, Ser. No. 08/491,946 filed Aug. 30, 1995 now U.S. Pat. No. 5,730,145 entitled An Interactive Respiratory Regulator.

BACKGROUND OF THE INVENTION

1. Field of the Invention

The invention relates to an interactive respiratory regulator comprising:

- a recording device recording the respiratory pattern of a user and producing a corresponding respiratory signal,
- an instruction signal generator for generating an instruction signal that can be perceived by the user in order to influence his respiratory behavior,
- a control device controlling the instruction signal generator,
- a processing device which determines by means of a parameter of the respiratory signal received whether the respiratory pattern recorded during a predetermined time span meets a pre-adjustable standard for this parameter, and which at a certain error percentage sends a starting signal to the control device.

2. Description of Related Art

An apparatus of this kind, indicating to a user a desirable respiratory pattern, is known from the Netherlands patent specification 166.850, whereby this apparatus, In particular to combat the hyperventilation syndrome, is provided with a device for determining the cycle time. The corresponding frequency of the respiratory cycles is applied as parameter for the respiratory pattern. The recording device, being for instance a strain gauge or a mercury wire recorder applied to the chest of the user, produces a pulse signal with a repeat frequency corresponding with the respiratory frequency. This signal is fed to a time-determining device which compares this frequency with a present standard or limit value. As soon as this processing device determines that the respiratory frequency is higher than the limit frequency it will set off a sound generator which during each respiratory cycle produces two, for the patient audible and differentiable tones.

However, not only patients suffering from hyperventilation, the symptom of which is an abnormally high respiratory frequency, exhibit a non-optimal respiratory behavior, but also users who suffer, for instance, from phobias or psychic traumas of any kind.

Describing the pattern of such a non-optimal respiration solely in terms of respiration frequency was shown not always to be adequate. The present invention ensues from the search for a useful, instructive feedback to the user with non-optimal respiratory patterns including others besides those which occur through hyperventilation. On these grounds it has been concluded that in order to analyze a respiratory pattern correctly, knowledge of especially the ratio between the in- and exhalation times is indispensable. The pause after exhalation is also an important parameter.

The known apparatus described above has, however, the limitation that it does not include that necessary extra information in the feedback process, thus offering insufficient possibilities for application to remedy disorders or to correct deficient respiratory patterns in general.

SUMMARY OF THE INVENTION

The object of the invention is to provide an apparatus in accordance with the kind mentioned in the preamble, which analyzes a user's recorded respiratory pattern in more detail and which not only tests a threshold with respect to the respiratory frequency.

To this end the interactive respiratory regulator according to the invention is characterized in that the processing device processes as parameter the ratio between the in- and exhalation time in a respiratory cycle, and optionally the pause after exhalation.

In a preferred embodiment the processing device includes the frequency of the respiratory cycles as a second parameter and the pre-adjustable standard also comprises a value for this parameter.

This apparatus can offer the user suffering from any kind of stress dependant respiratory regularity disorders the advantage of useful feedback. Thus, the apparatus offers a wide range of applicability not only with hyperventilation, but in principle with any non-optimal respiratory behavior. The interactive respiratory regulator can, for instance, also be used by people who, especially in the case of continual stress, wish to acquire a healthy manner of respiration.

The invention also relates to a recording device for the recordal of movements of parts of the body, particularly for the use in an interactive respiratory regulator according to the invention. The recording device is characterized in that the respective parameter error signals are fed to a decision device, the output signal of which is fed to the control device as a starting signal.

Preferably the recording device determines the values of the various parameters of the movement pattern from the frequency changes of the sound impulses during each cycle of movement. In this way the system can put into practice effectively, without sensitivity to interferences and with a very short setting time, without adjusting the length of the tube to the circumference of the user's chest.

The interactive respiratory regulator according to the invention will be described below on the basis of an embodiment example referring to the accompanying drawing.

DESCRIPTION OF THE PREFERRED EMBODIMENT

Figure 1:
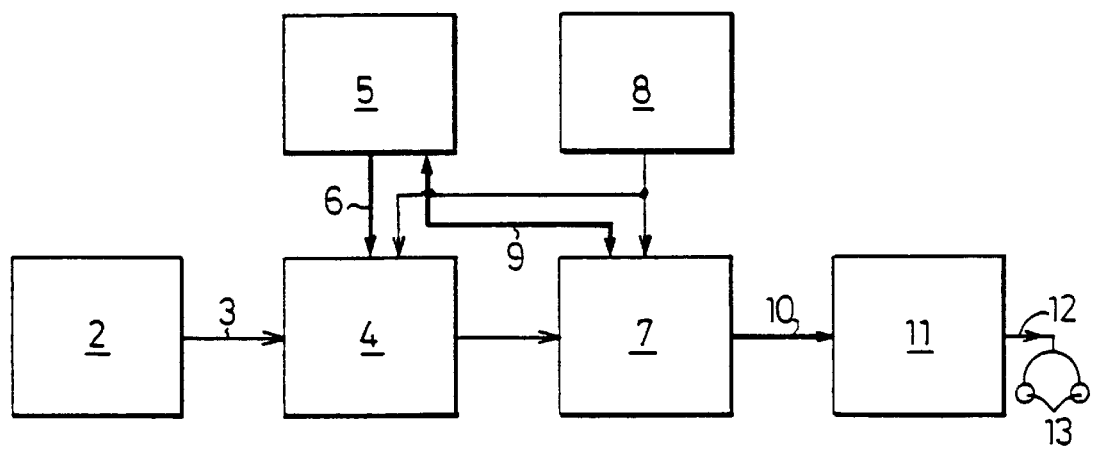
FIG. 1 is a general block diagram of a preferred embodiment of the interactive respiratory regulator in accordance with the invention.

As shown in FIG. 1 the interactive respiratory regulator 1 comprises a recording device 2, recording the user's respiratory movement and transducing this into an electrical, for instance digital respiratory signal 3, which is fed into a processing device 4.

In this processing device 4 the characteristic parameters such as cycle duration, the ratio between the in- and exhalation time during a respiratory cycle and optionally the pause after exhalation of the respiratory signal 3 thus received are then determined and compared with standard values that have previously been programmed into a memory 5 and can be read via a data path 6. If during a predetermined time span one or more parameters do not come up to the standard values, the processing device 4 will, at a certain maximal error percentage, send a starting signal to control device 7. This control device 7 is also connected to the memory 5 and is, just as the processing device 4, controlled by a clock signal sent by the clock generator 8.

Via a data path 9 the control device 7 reads information, corresponding to the standard values from the memory 5 and feeds these via a data path 10 into an instruction signal generator 11. From this information said generator then compiles an optimized respiratory pattern which serves to instruct the user with the object of influencing his respiratory behavior.

This optimized respiratory pattern is issued in the form of an instruction signal 12, for instance a sound signal conveyed via a headphone 13. This can, for example, consist of two. distinguishable tones of different pitch per respiratory cycle, as is illustrated very schematically in FIG. 3. If the user follows these respiratory instructions, the corrected respiratory behavior will eventually lead to a desired improvement of his physiological condition. As soon as the respiratory pattern, which is constantly recorded by the recording device 2, once more meets the above-mentioned parameter standards, the processing device 4 will remove the starting signal to the control device 7, when the generator 11, possibly after a certain delay or learning period, will stop issuing the instruction signal 12.

Figure 2:
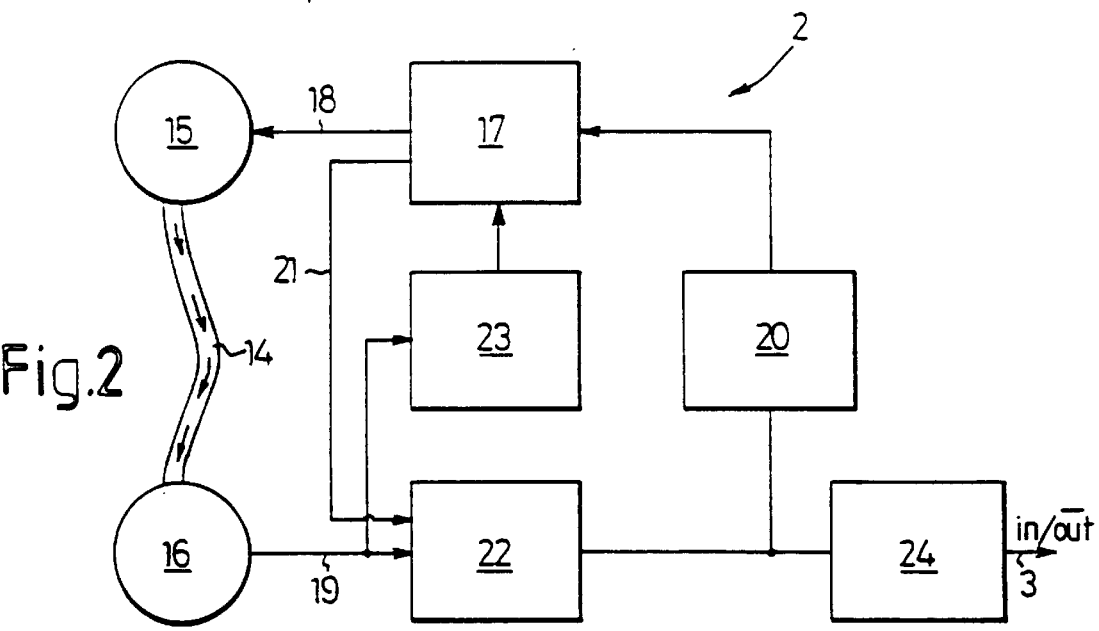
FIG. 2 is a block diagram of the recording device of FIG. 1.

The recording device 2 which is shown schematically in FIG. 2, comprises in a special embodiment an elastic hollow tube 14, stretched around the chest or abdomen of the user, forming the measuring distance of the recording device 2. At the two ends of the tube 14 electro-acoustic transducers 15, 16 are mounted to generate, respectively receive, sound impulses transmitted through the tube 14. The sound impulse sender 15 transduces electrical signals 18 emitted by an impulse generator 17 into sound impulses which in a certain transit time pass through the length of tube 14 and are subsequently received by the receiver 16. Said receiver then transduces the sound impulses into electrical signals 19, which are fed back preferably via a frequency regulation device 20 to the impulse generator 17. This feed-back, preferably in the form of a phase-locked loop, occurs such that the repeat frequency f of the sound impulses is inversely proportional to the length L of the tube 14. Thus the length of the tube 14 can be directly deduced from this sound impulse frequency and consequently also the changes therein caused by the respiratory movements of the user.

The transit time of the sound impulses is determined by the length of the tube 14, which will vary due to the respiratory movements. During one in- and exhalation, the length of the tube will increase, respectively decrease and consequently a sound impulse will be received at a relatively earlier, respectively later moment in time. The moment of reception is compared with a reference impulse signal 21 issued simultaneously by the impulse generator 17. The time and phase difference with respect thereto is determined by a phase difference detector 22, determining the extent of the phase difference as well as its character, that is to say, it will determine whether the impulse signal 19 received lags behind the reference pulse signal 21 (inhalation) or runs ahead of it (exhalation).

In order to guarantee a stable phase relation between the reference impulse signal 21 and the received pulse signal 19, in other words in order to maintain the relation f-1/L, the repeat frequency f of the Pulse signal produced by tale pulse generator 17 must be adjusted after each pulse cycle. This is preferably done, as already mentioned, by means of a phase-locked loop, to which end the frequency regulation device 20 is among other things equipped with a filter, an integrator and a voltage-controlled oscillator, which, however, for the sake of simplicity are not shown in the block diagram of FIG. 2. In this way the pulse frequency f of the electrical pulse signal generated by the generator 17 is regulated such that in case of a longer or shorter length of tube 14 the pulse frequency f is lowered, respectively raised by means of said regulation loop. In this manner the phase relation between the received signals and the reference pulse signals 19 respectively 21 at the beginning of each pulse cycle are stabilized, irrespective of the extent to which the tube 14 is stretched.

In order to also keep the sound pulses, weakened by transmission losses in the tube 14, at a constant intensity, independent of the length of the tube 14, the received pulse signal 19 is at the same time fed back into the pulse generator 17 via an amplitude regulation device 23, effectuating a constant amplitude of the pulse signal.

It will be understood that the recording device 2 is completely self adjusting so that it can be equipped with, for instance a removable and easily deformable tube 14 of any length which does not need to be adapted to the chest circumference of the user. The tube 14 can therefore easily be applied by the user himself, without any aids such as adhesive, adhesive tape or adhesive electrodes, if desired even over the clothing of the user. Exchange of the recording device 2 between users, female or male, is also no problem. The electro-acoustic transducers 15, 16 can, for instance, be housed in a housing which can serve as coupling piece for connecting the ends of the tube 14 and the necessary electric wiring.

Figure 3:
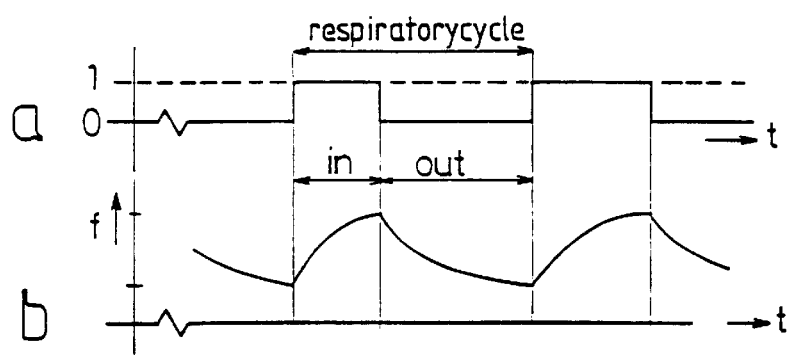
FIG. 3a is an amplitude-time diagram of the respiratory signal of FIG. 1 produced by the recording device.
FIG. 3b is an example, very schematically illustrated, of a frequency-time diagram of the instruction signal emitted by the instruction signal emitted by the instruction signal generator.

The signal issued by the phase difference detector 22 is fed into a respiratory pattern analyzer 24 which by means of the phase difference signal analyzes the recorded respiratory pattern, passing the same in the form of a respiratory signal 2, for instance, in digital form as is shown in FIG. 3, to the processing device 4.

Figure 4:
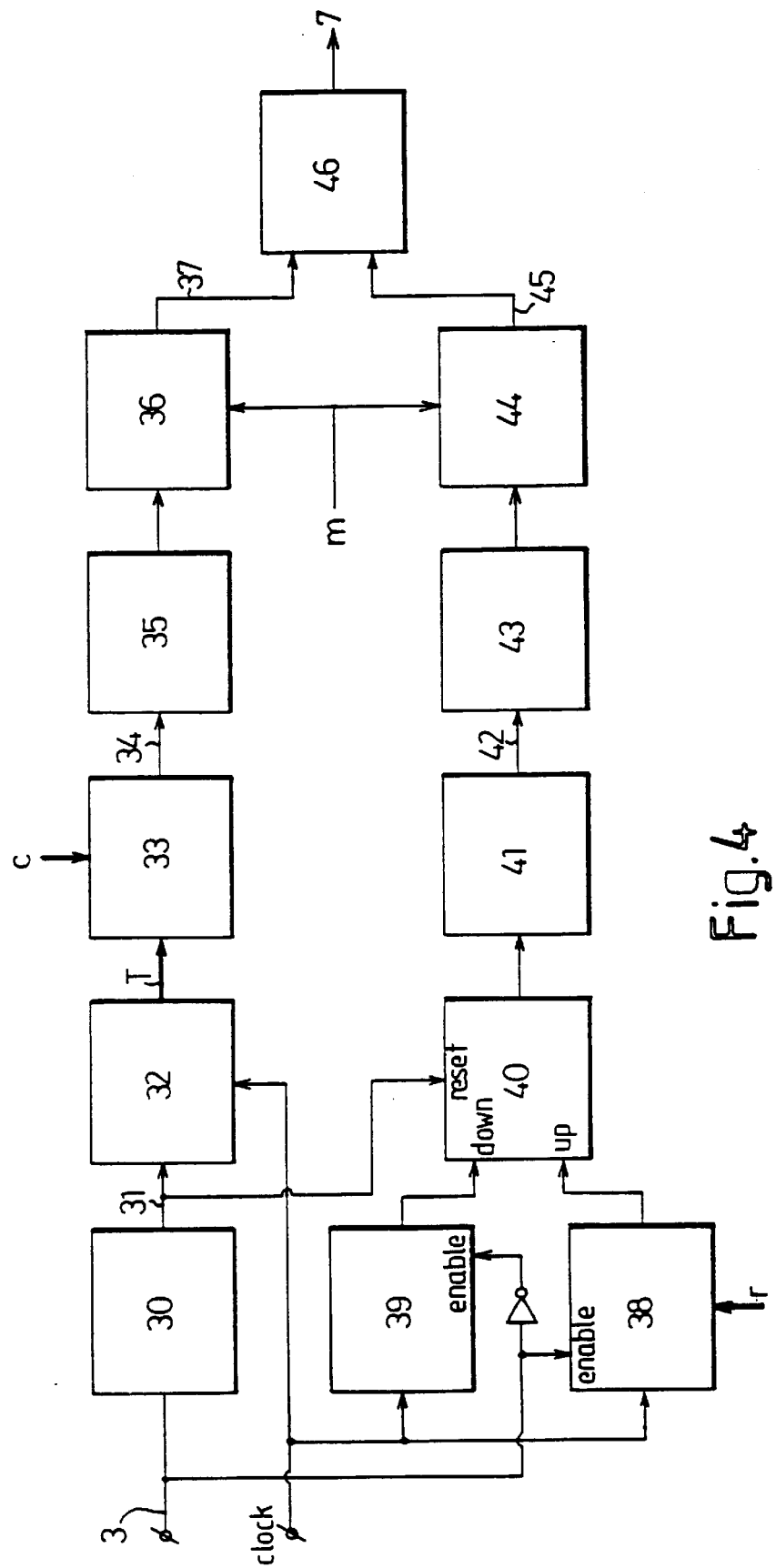
FIG. 4 is a block diagram of the processing device of FIG. 1.

This processing device 4 is shown in a very simple basic form in FIG. 4. It comprises a cycle detector 30 which at the beginning of each respiratory cycle defined as the moment at which an inhalation commences, issues a cycle pulse 31, resetting and starting a controlled cycle time counter 32 coming from the clock signal of the clock generator 8 (see FIG. 1). A cycle time comparator 33 compares constantly the count T of the cycle counter 32 with a cycle time standard value c, read from the memory 5. As soon as T reaches the value c, the comparator 33 issues a cycle time go-signal 34 which is fed into a time averaging device 35. During a preset period of time said device will determine the average and will feed this into a comparator 36, which, if this average number is below a certain minimum percentage m, will issue a cycle time error signal 37.

In the lower branch of FIG. 4 the ratio between the in- and exhalation time during each respiratory cycle is evaluated at the same time.

For this purpose there are preferably two frequency dividers 38 and 39 included, which are both controlled by the clock signal with the frequency F. During each inhalation the frequency divider 38, enabled by the respiratory signal 3, issues a pulse signal with frequency F R/10, whereby R is a value read from the memory 5 equal to five times the ratio's standard value r, to an adder entry of a ratio counter 40, which is reset at the beginning of each cycle. On the other hand, the frequency divider 39 enabled by the inverted respiratory signal 3 sends during each exhalation a pulse signal with frequency F/2 to a deduction entry of the ratio counter 40. When, after successively adding or deducting the count of the ratio counter 40 has reached the value zero, that is to say as soon as the exhalation time is at least equal to the inhalation time multiplied by a factor r, then a ratio comparator 41, being in fact a zero detector, sends a ratio go-signal 42, resulting eventually via a time averaging device 43 and a comparator 44 in a ratio error signal 45, if the average number of ratio errors is too high.

The cycle time and ratio error signals 37, 45 are fed to a decision device 46, which, for instance carries out a logical or function and issues the starting signal if one or more error signals are active.

It will be clear to an expert in the field of electronic circuits that the principle described above can, of course, be carried out in many other ways. Especially with the current microprocessor techniques the processing device 4 can in an alternative embodiment be provided with a processing unit with a memory in which a computer program is stored. This program can then determine in real-time the cycle time and the ratio between the in- and exhalation time from the respiratory signal 3; can compare these parameters with selected standard values; can average the result of these comparisons over a predetermined time; and can cause the issue of a starting signal dependent on a predetermined decision criterium to the control device 7.

Figure 5:
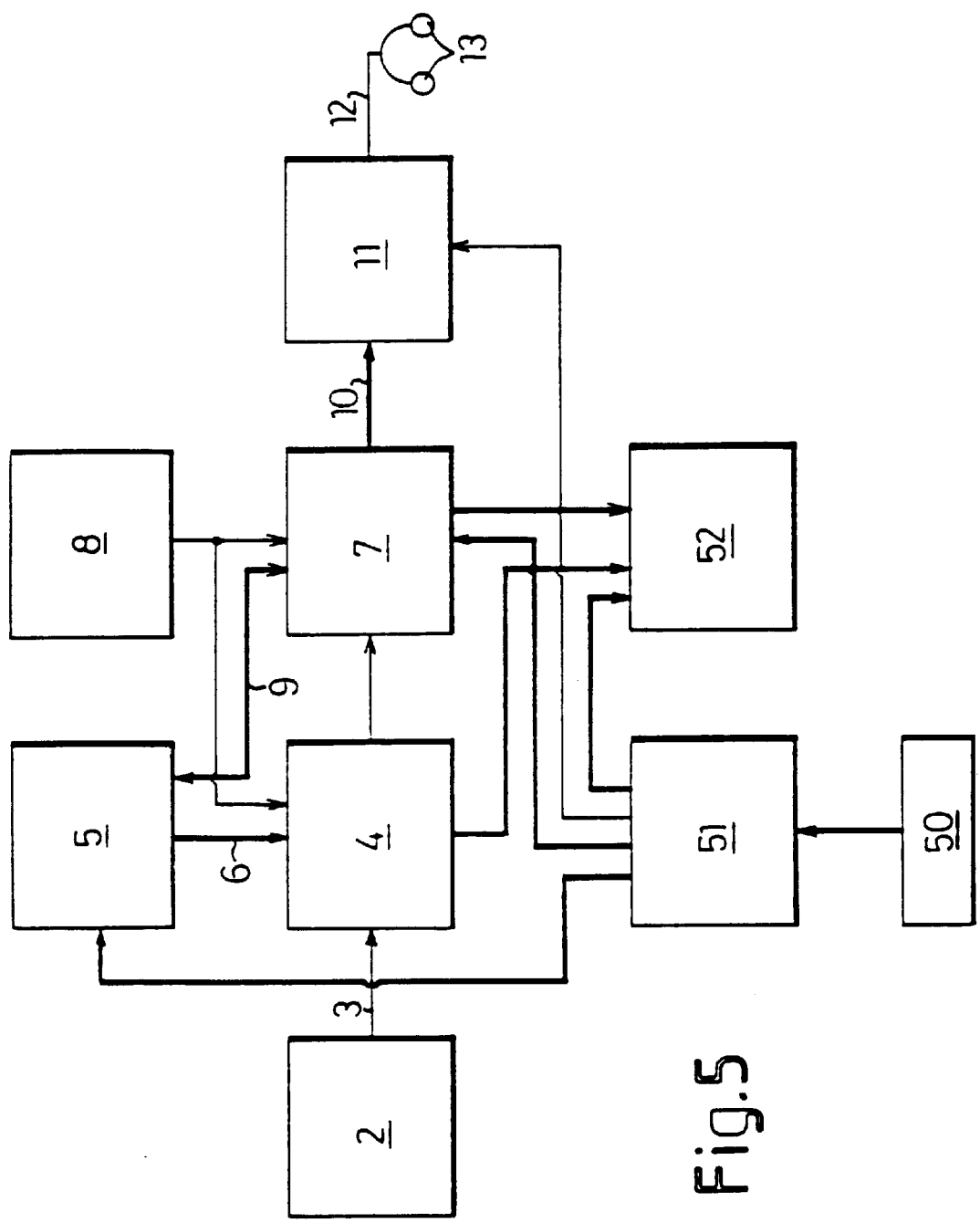
FIG. 5 is a block diagram corresponding to FIG. 1 comprising in addition an operating device and display unit.

The interactive respiratory regulator 1 possesses at least two action modes, viz. a programming mode and a feedback mode. During the feedback mode the recording device 2 records the respiratory pattern of the user and the instruction signal generator 11 sends him, if necessary, instruction signals 12. During the programming mode the instruction signal generator 11 is blocked and the possibility exists to select via an operating device 51 equipped with a keyboard 50, as shown in FIG. 5, a combination of one or more parameter conditions and a corresponding respiratory pattern. These parameter standards and respiratory pattern information are, as already mentioned, stored in the memory 5 and correspond with each other in the form of a number of series of respiratory patterns and parameter conditions specifically geared to them. In this manner the user and/or the treating therapist may choose from a number of respiratory instruction programs, each of which comprises a respiratory pattern to be synthesized with the corresponding standard values.

The respiratory pattern information stored In the memory 5 relates to the in- and exhalation times, the in- and exhalation rate and/or the pauses following the in- and exhalations. These parameters are expressed by the instruction signal generator 11 in the form of changes in the duration and the pitch of the zone of the instruction signal 12. Particularly instructive is, for instance, a tone increasing in pitch to indicate an inhalation, respectively, a tone decreasing pitch to indicate an exhalation (see FIG. 3b).

To this purpose the control device 7 reads said information via a data path 9 from the memory 5 and passes this via a data path 10 on to the instruction signal generator 11. Said generator uses the information in the feed back mode, if the starting signal is active, to synthesize the desired respiratory pattern. Its characteristics are thus determined by choice through the information selected from the memory with the keyboard 50.

Data regarding the selected respiratory feed-back program can be shown during programming, preferably via a display unit 52, illustrated in FIG. 5. This display unit 52 can also show, for instance during a special instruction mode, the parameters of the currently recorded respiratory pattern for the purpose of an optical feedback to the user or for instance the therapist, to make a diagnosis.

In order finally to allow the user or the person susceptible to stress to become accustomed to the instruction signals, it is also possible to provide a teaching mode. During this teaching mode the instruction signal 12 is issued by the instruction signal generator 11 independently of the starting signal. The choice between the different modes is simply made via the key board 50.

Figure 6:
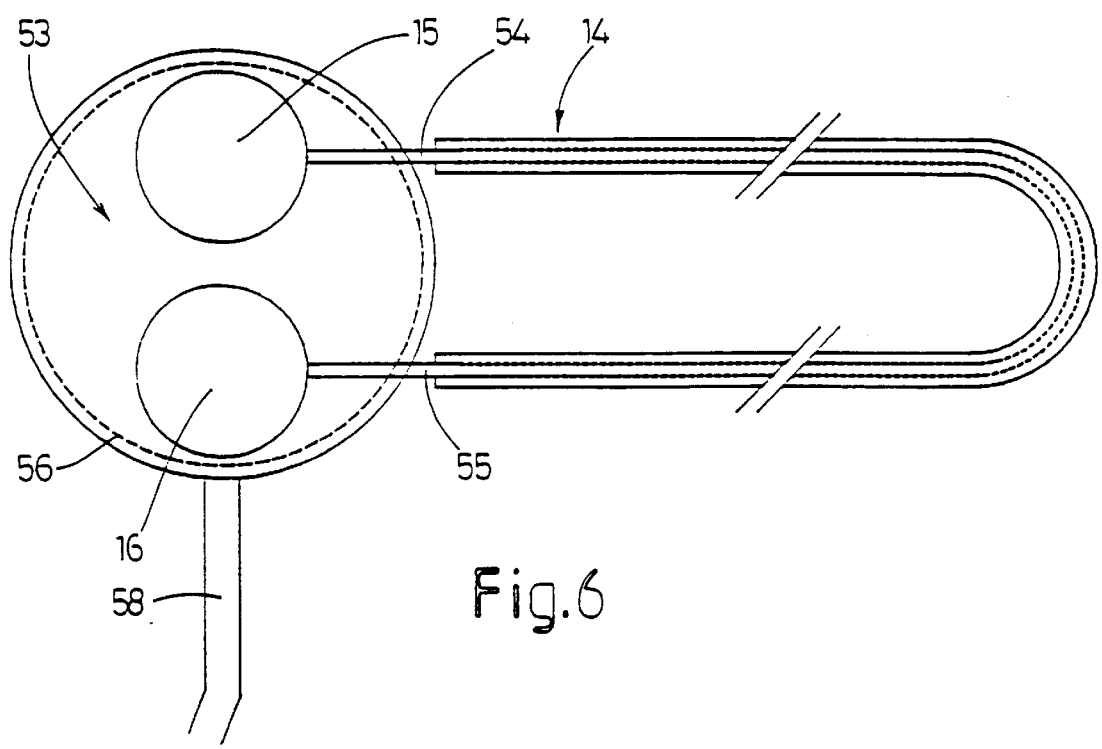
FIG. 6 is a schematic frontal view of the recording device.

The display unit schematically shown in FIG. 6 comprises the housing 53 in which the electro-acoustic transducers 15, 16 are housed. One of these electro-acoustic transducers 15, 16 functions as source, the other as receiver unit. The electro-acoustic transducers 15, 16 are connected with each other via the elastic tube 14, which is made, for instance from silicone polymers. The connection between the tube 14 and the electro-acoustic transducers 15, 16 can be made by means of the tube connectors 54, 55 mounted in the housing.

For securing to chest or abdomen with the aid of the tube 14, the housing can be provided with a fastening notch 56, extending for example over 180° or more over the circumference of the housing.

Figure 7:
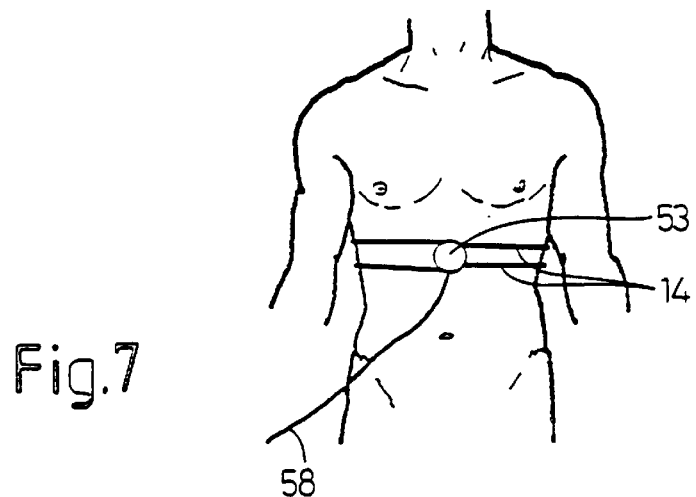
FIG. 7 is an illustration of a recording device applied to a user's chest.

As mentioned above, the electro-acoustic transducers 15, 16 may be housed in a housing. This housing may have the form of a clasp, whereby the tube 14 is formed into a single large loop and is stretched double around the chest and/or abdomen. This is shown in FIG. 7, whereby the tube 14 is stretched in a double loop around a person's chest and the housing 53 functions as clasp. The tube 14 is brought over an operable distance into the fastening notch 56. The connecting lead 58 leads from the housing to the processing device 4 (not shown).

According to a favorable embodiment the interactive respiratory regulator is executed in the form of an automatic device comprising a control program and predetermined standard values. Dependent on the user, for example, in the case of children or patients such as stress patients, trauma patients, one may deviate from the fixed standard values, the respiratory regulator exactly controls the respiration in correspondence with the parameters (frequency, ratio, pause) incorporated in the standard values. This enables the user, without help from a doctor or expert, to operate and use the respiratory regulator, which was not possible with the respiratory regulators according to the prior art.

Figure 8:
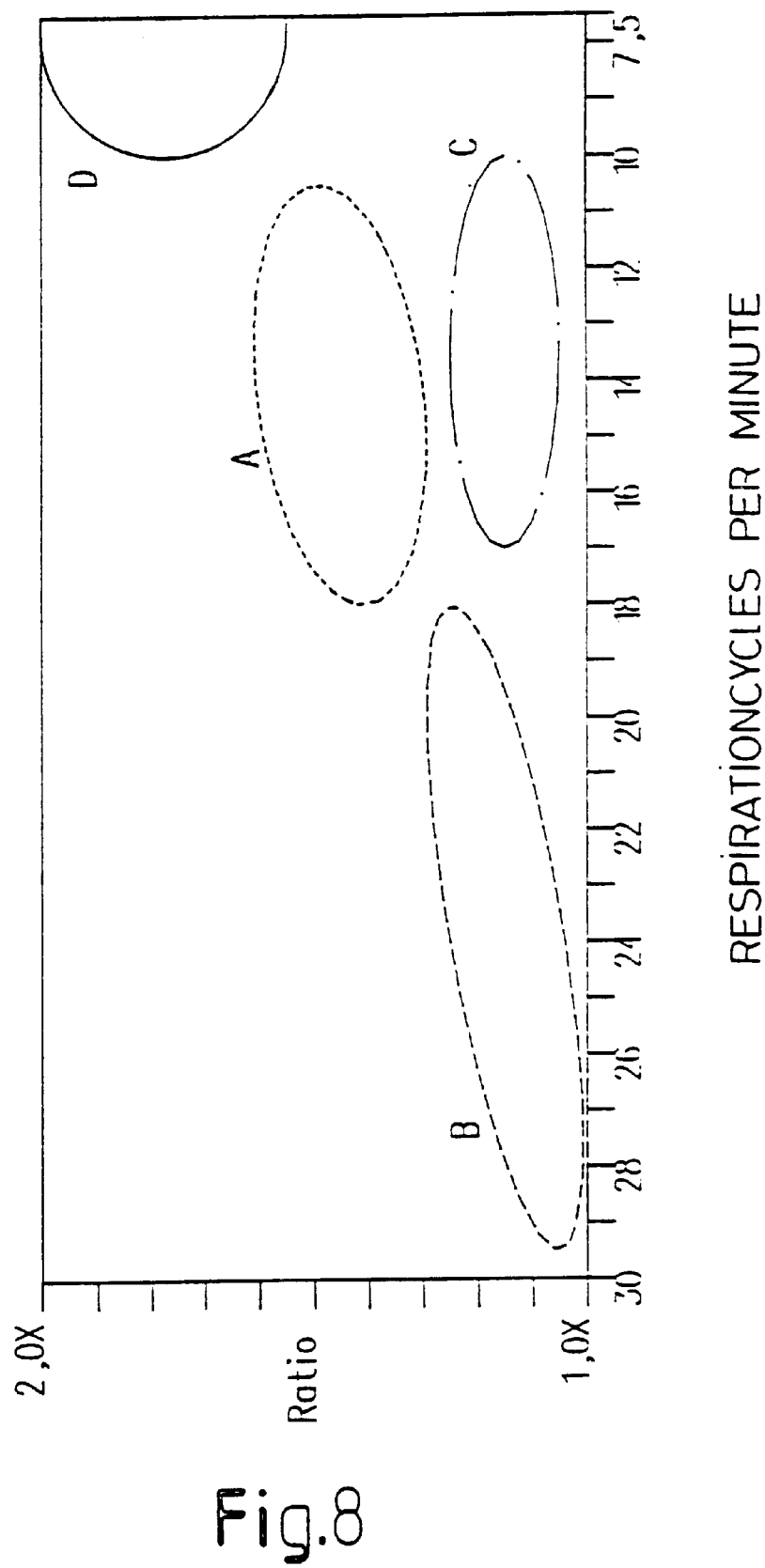
FIG. 8 is a graphic representation of the number of respirations per minute plotted against the ratio of the in- and exhalation time for different groups of users.

In FIG. 8 the ratio R, being the inhalation time divided by the exhalation time, is plotted against the number of respirations per minute. This gives a different picture for different user groups. Field A, indicated by a discontinuous line, comprises normal, healthy adults while field D, indicated by a continuous line, shows the level of respiration achieved by people going in for sports and yoga. Individuals with irregular respiration are found in field C, indicated by a dot-dash line. Individuals who hyperventilate are found in field S. For children whose chests are not yet full-grown, a similar graph can be made. Thus, the apparatus according to the invention also allows a diagnosis Lo be made. in addition, the apparatus can be used for therapeutic purposes without any further adaptations. Apart from regulating deficient respiratory patterns the apparatus according co the invention was also shown to help people who, through traumatic experiences in the past and in spite of psychotherapy or relaxation exercises, were unable to breathe in a healthy, regular manner, to breathe calmly and controlled within 5–10 minutes. In this way it was possible to achieve a deep relaxation much faster than when using apparatuses according to the prior art, which has a very favorable effect on coping with psychic traumas.

We claim:

1. An interactive respiratory regulator for a user having a body and a respiratory pattern and cycle possessing an inhalation and exhalation time having a ratio thereof, a pause being present after exhalation, comprising:

a recording device recording the respiratory pattern of a user and producing a corresponding respiratory signal, an instruction signal generator for generating an instruction signal that can be perceived by an user in order to influence his respiratory behavior, a control device controlling the instruction signal generator, a processing device which determines by means of a parameter of the respiratory signal received whether the respiratory pattern recorded during a predetermined time span meets a preadjustable standard for this parameter, and which at certain error percentage sends a starting signal to the control device, the processing device (4) processes as parameter the ratio between the inhalation and exhalation time in a respiratory cycle, and optionally uses the pause after exhalation.

2. An apparatus according to claim 1, whereby respiratory cycles have a frequency, the frequency of the respiratory cycles is measured, wherein the processing device (4) processes the frequency of the respiratory cycles as second parameter and that the pre-adjustable standard also comprises a value for this parameter.

3. An apparatus according to claim 2, wherein the respiratory signal is fed to a clock generator controlled counter and a comparator, which during each respiratory cycle, when a count corresponding with a parameter standard is reached, issues an output signal to a time averaging device, wherein the processing device (4) is provided with at least two such counters (32, 40), comparators (33, 41) and time averaging devices (35, 43) allotted to each parameter, whereby each comparator (33, 41) sends a parameter O.K. signal (34, 42) to be fed to a time averaging device (35, 43), as soon as the corresponding counter (32, 40) has reached a count corresponding with the respective parameter standard.

4. An apparatus according to claim 3, wherein the counter (40), in order to compare the ratio between the inhalation and exhalation time with the standard, adds during an inhalation and deducts during an exhalation.

5. An apparatus according to claim 4, wherein during a predetermined period of time each time averaging device (35, 43) will determine a percentage of faulty respiratory cycles where the relevant parameter does not comply with the corresponding parameter standard, and that each time averaging device (35, 43) is connected to comparator (36, 44) recording any parameter error signal (37, 45) as soon as an average error percentage for that parameter exceeds a preset value.

6. An apparatus according to claim 5, wherein respective parameter error signals (37, 45) are fed into a decision device (46), the output signal of which is fed into the control device (7) as starting signal.

7. An apparatus according to claim 6, wherein a decision organ (46) carries out a logical function.

8. An apparatus according to claim 2, wherein the processing device (4) is provided with a processing unit having a memory, in which a computer program is stored, which on execution determines from the respiratory signal (3) the time of the cycle and/or the ratio between the inhalation and exhalation times in real-time, compares these parameters with (a) standard value(s) selected for this purpose, averages results of these comparisons over a predetermined period of time and causes a starting signal to be sent to the control device (7), in accordance with a predetermined decision criterium.

9. An apparatus according to claim 8 wherein various parameter standards and information relating to a desired synthesizable respiratory pattern are stored in a memory (5) and are selectable in a program mode, during which the instruction signal generator (ii) is disabled.

10. An apparatus according to claim 9, wherein memory (5) comprises a number of parameter standards and corresponding respiratory pattern information.

11. An apparatus according to claim 10, wherein respiratory pattern information relates to the inhalation and exhalation times, the inhalation and exhalation rates and/or the pauses following the inhalation and exhalations of the desired synthesizable respiratory pattern.

12. An apparatus according to claim 11, wherein when the starting signal is active, the instruction signal generator (11) compiles in a feedback mode the desired synthesizable respiratory pattern of the respiratory pattern information which the control device (7) reads from the memory (5).

13. An apparatus according to claim 12, wherein it comprises an operating device (51) equipped with a key board (50), by which means switching between different modes, selection of the standards stored in the memory (5) and respiratory pattern information and/or volume regulation of the instruction signal (12) is possible.

14. An apparatus according to claim 13, wherein it is further provided with a display unit (52), by which means current mode, the selected standards and the respiratory pattern information and/or the instruction signal volume can be visualized.

15. An apparatus according to claim 14, wherein the display unit (52) in the feedback mode also displays information sent by the processing device (4) concerning parameters of a currently recorded respiratory pattern.

* * * * *